United States Patent [19]

Schmid et al.

[11] Patent Number: 5,248,602
[45] Date of Patent: Sep. 28, 1993

[54] PROCESS AND INSTALLATION FOR THE UTILIZATION OF ORGANIC SUBSTANCES

[75] Inventors: Walter Schmid, Püntenstrasse 5, CH-8152 Opfikon; Christian Widmer, Basel; Arthur Wellinger, Guntershausen, all of Switzerland

[73] Assignee: Walter Schmid, Opfikon, Switzerland

[21] Appl. No.: 682,755

[22] Filed: Apr. 9, 1991

[30] Foreign Application Priority Data

Sep. 18, 1990 [CH] Switzerland ............ 03015/90

[51] Int. Cl.$^5$ .................. C05F 11/08; C12P 5/02; C12P 1/04; C02F 11/04
[52] U.S. Cl. ......................... 435/170; 71/10; 210/602; 210/603; 210/613; 435/167; 435/310; 435/316; 435/813
[58] Field of Search ............ 210/602, 603, 613; 435/167, 170, 310, 813, 316; 71/10

[56] References Cited

U.S. PATENT DOCUMENTS

| | | | |
|---|---|---|---|
| 3,711,392 | 1/1973 | Metzger | 435/167 |
| 4,053,394 | 10/1977 | Fisk | 210/606 |
| 4,511,370 | 4/1985 | Hunziker et al. | 435/801 |
| 4,684,468 | 8/1987 | De Baere | 435/167 |

Primary Examiner—Herbert J. Lilling
Attorney, Agent, or Firm—EGLI International

[57] ABSTRACT

A process and an installation for utilizing organic substances are proposed, in which the substances are correspondingly comminuted and processed by mixing and reaction stages to utilizable compost.

The installation essentially comprises a heatable fermenter with a stirrer located therein. In order to obtain an approximately closed process circuit the comminuted substances are supplied as so-called fresh material by a supply shaft to a conveying shaft constructed as a heat exchanger and undergo corresponding heating therein. Through further supply of fresh material the already heated fresh material is supplied to the fermenter and mixed therein by the stirrer accompanied by further heating.

The fermented matter formed in the fermenter, on supplying further fresh material, can be admixed in a specific ratio as so-called bacterial inoculum with the fresh material throughout the process circuit.

The gases formed during the fermentation process in the tank can either be used in the installation as process energy or can be supplied via a line to another energy supply plant.

4 Claims, 2 Drawing Sheets

PROCESS AND INSTALLATION FOR THE UTILIZATION OF ORGANIC SUBSTANCES

BACKGROUND OF THE INVENTION

1. Field of the Invention

The invention relates to a process for the utilization of organic substances, as well as to an installation for performing the process, in which the organic substances are comminuted and processed by corresponding mixing and reaction stages in reaction chambers to a utilizable compost.

2. Discussion of the Prior Art

DE-A-31 52 609 discloses a process for the utilization of domestic refuse and other organic substances, in which the delivered domestic refuse is separated in an associated sorting or grading installation from the inorganic substances, such as e.g. glass, plastics, metals, etc. The organic substances are supplied by means of a conveyor belt to a metering or dosing apparatus and from there to a mixing tank, in which the substances are correspondingly mixed by a stirrer, accompanied by the supply of liquid. The substances are then supplied via a crusher and comminuter to a waiting tank, in which methane gas is supplied to the organic substance. The oxygen-freed mixture is subsequently conveyed via a heat exchanger into a reaction container, in which the decomposition of the organic substances essentially takes place by bacteria. The aforementioned process and the installation for performing the same is essentially used for the recovery of methane gas by the bacterial decomposition of organic waste.

SUMMARY OF THE INVENTION

The present invention deals with the problem of an economic reutilization of organic substances, such as those caused e.g. by humans and animals, the problem of the invention being to develop a process and an installation for performing the process, in which the organic substances are processed by an effective, environmentally friendly decomposition operation to a material, such as can e.g. be processed as an additive for compost, garden mould, etc.

According to the inventive process this problem is solved in that the comminuted, organic substances in compressed form are supplied as fresh material to a conveying shaft constructed as a heat exchanger and are heated therein to a process temperature dependent on the fresh material, that by further supply of fresh material to the conveying shaft simultaneously the already heated fresh material is supplied to a heated fermenter for a fermentation process and is mixed by a stirrer, accompanied by the simultaneous removal of the gases which form and, up to the end of the overall process, the fermented matter produced in the fermenter is, as desired, admixed as a bacterial inoculum in a specific ratio with the fresh material suppliable to the conveying shaft.

The inventive installation for performing the process comprises a tank or fermenter and a stirrer located therein and is characterized in that a supply shaft and a heatable conveying shaft, as well as a correspondingly constructed discharge apparatus are provided, being connected to the container or fermenter in such a way that at least the supply shaft and the conveying shaft form together with the fermenter a closed process circuit, which is controllable for a predetermined supply of fresh material, as well as fermented matter as a bacterial inoculum by means of correspondingly positioned locks or sluices.

BRIEF DESCRIPTION OF THE DRAWINGS

Further features of the invention can be gathered from the following description in conjunction with the embodiments shown in the drawings and the claims. The invention is described hereinafter relative to the drawings, wherein show:

DESCRIPTION OF THE PREFERRED EMBODIMENTS

Figure 1:
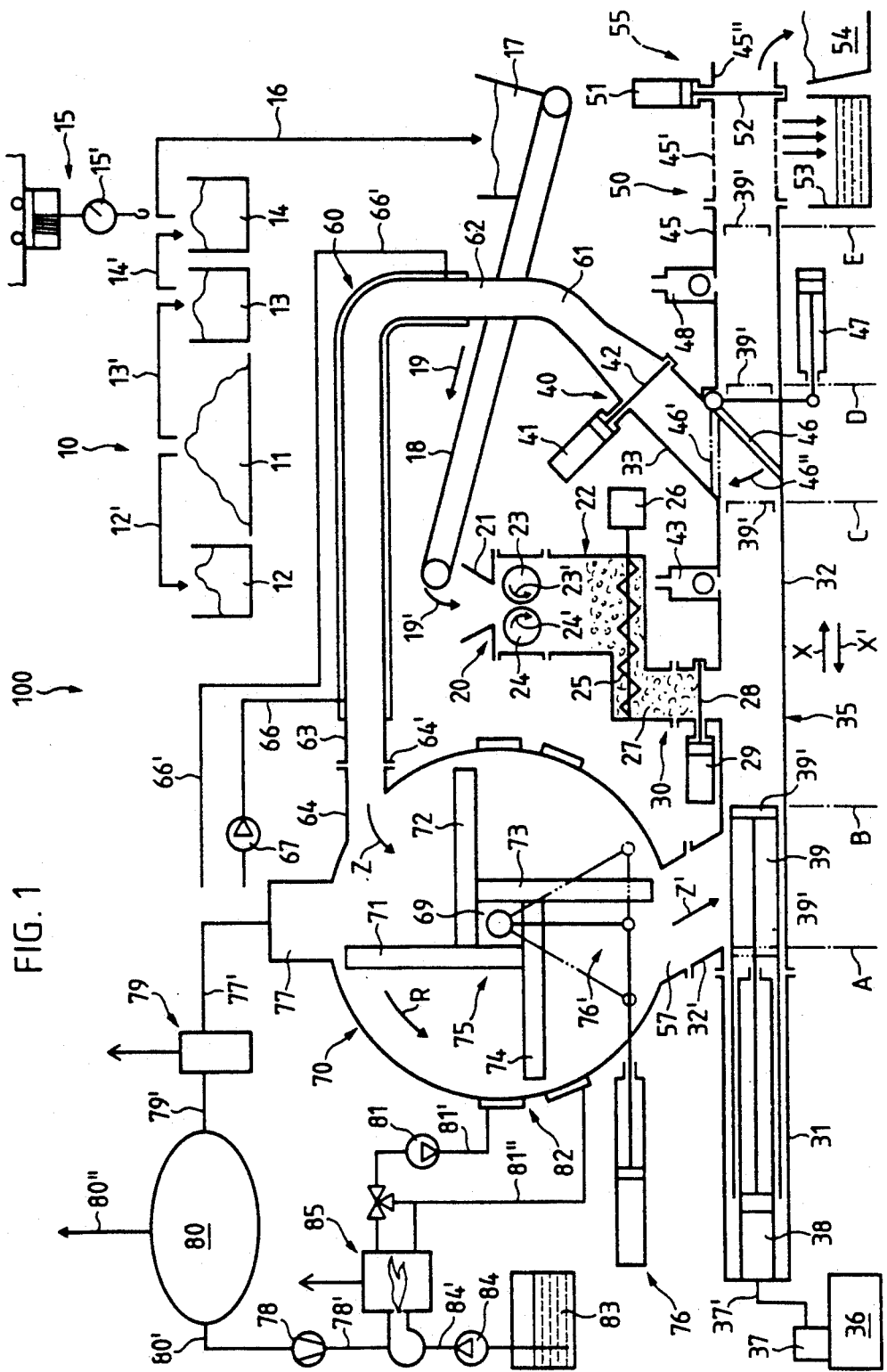
FIG. 1 a first embodiment, shown as an overall view, of an installation for processing and utilizing organic substances represented as a flow diagram.
Figure 2:
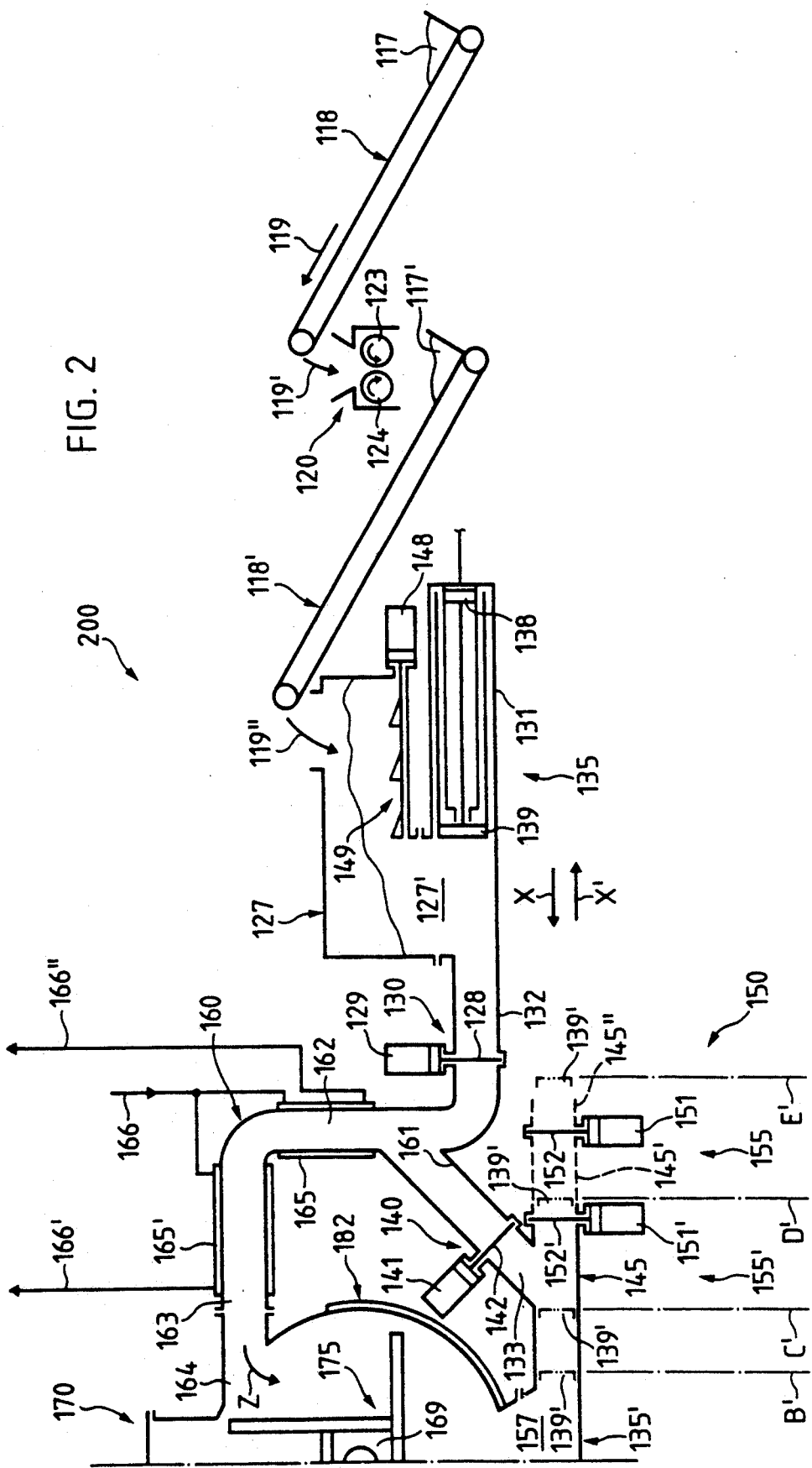
FIG. 2 a portion of a second embodiment of an installation for procesing and utilizing organic substances represented as a flow diagram.

FIG. 1 shows as a first embodiment an installation substantially represented as a flow diagram and given the overall reference numeral 100, whilst FIG. 2 shows a portion of the installation 200. The two installations 100 and 200 constructed for the processing and utilization of organic substances are described in detail hereinafter. Subsequently a description will be given of the operation of the two installations 100 and 200.

The installation 100 essentially comprises a sorting or grading apparatus 10, a comminuting apparatus 20, a supply shaft 35, a discharge apparatus 50, a conveying shaft 60, a tank or fermenter 70 equipped with a stirrer 75, a boiler 85 associated with the fermenter 70 and a tank 80 constructed as an intermediate gas reservoir. The aforementioned components are described in detail hereinafter.

The sorting apparatus 10 has an e.g. container-like collecting station 11, as well as correspondingly associated tanks 12,13 and 14. In the collecting station 11 the substances which may be e.g. supplied in plastic bags or loose are sorted by not shown means or also manually into organic and inorganic substances.

The inorganic substances, e.g. impurities and inhibitors are supplied in the direction of arrow 12' to the tank 12 and from there to a not shown dump for a different processing or destruction. The inorganic substances can be destroyed e.g. in a not shown combustion or incineration plant.

The sorted, organic substances are supplied in the direction of arrow 13' to the tank 13 in the form of an intermediate storage means and from there in the direction of arrow 14' to the tank 14. However, the organic substances can also be supplied directly from the collecting station 11 to the tank 14.

By means of a correspondingly associated conveyor 15 the organic substances are supplied by the tank 14 in the direction of arrow 16 to a further tank 17 in operative connection with a conveyor belt 18. The conveyor 15 is e.g. provided with a correspondingly constructed balance 15' by means of which the organic substances can be subdivided into specific quantities, e.g. into corresponding daily portions for processing. These daily portions are then supplied to the tank 17.

By at least one conveyor belt 18 associated with the tank 17 the organic substances are su plied in the direction of arrows 19,19' to the comminuting apparatus 20 associated with the conveyor belt. The comminuting apparatus 20 comprises a tank 22 having a hopper 21, in which in the upper region are located at a limited distance from one another two roll bodies 23,24.

On the outer circumference the roll bodies 23,24 are provided with not shown comminuting elements, by means of which the organic substances supplied in the direction of arrow 19' and from the hopper 21 inserted between the two roll bodies 23,24 undergo a corresponding comminution. In not shown manner, the two roll bodies 23,24 are mounted about the longitudinal axis thereof in the tank 22 and are driven by correspondingly associated, not shown driving motors or the like in contrarotating manner in the direction of arrows 23',24'.

In the lower region of the tank 22 is positioned and mounted at least one conveyor screw 25 driven by an associated motor 26. The conveyor screw 25 conveys and compresses the comminuted organic substances into a sluice or lock-like chamber 27 of the tank 22. The lower region of the chamber is closed by a closing element 28 constructed in slide-like manner and operable by a first piston-cylinder unit 29. The chamber 27 and the closing element 28, as well as the piston/cylinder unit 29 together form a first sluice or lock designated 30.

The first sluice 30 is connected to the channel-like supply shaft 35, which comprises a first portion 31, a second portion 32 connected in not shown manner thereto, as well as a third portion 33. In the first portion 31 of the supply shaft 35 is located a thrust element 39 in operative connection with a second piston/cylinder unit 38 and which by means of the latter is arranged so as to move in the direction of arrows X,X' in the supply shaft 35. The diagrammatically represented thrust element 39 is e.g. constructed as a piston pump and in not shown manner is operatively connected to a correspondingly associated hydraulic unit 36 and to a drive 37 via a line 37'.

The thrust element 39 is displaceably arranged in linear manner in the supply shaft 35 and by means of corresponding, not shown control elements integrated in the drive 37 can be positioned in different positions for different functional steps. The individual positions A,B,C,D and E of the thrust element 39 in the shaft portions 31,32, as well as in a shaft portion 45 of the discharge apparatus 50 are indicated by the thrust element leading edge 39' shown in broken line form. The individual positions A to E will be described in greater detail hereinafter in conjunction with the operation of the overall installation 100.

At one end of the second shaft portion 32 is provided a connecting piece 32' and spaced from the latter the third, upwardly sloping shaft portion 33. Considered in the axial direction, the discharge apparatus 50 constitutes the extension of the portion 32. A second sluice 40 is arranged on the third, upwardly sloping shaft portion 33 and comprises a second piston/cylinder unit 41 and a closing element 42 in operative connection with the latter. Between the connection of the first sluice 30 and the second sluice 40 a venting and ventilating valve 43 is located on the second shaft portion 32.

The discharge apparatus 50 comprises a pivotably mounted flap 46 positioned between the second shaft portion 32 and the shaft 45 and which is pivotable by a third piston/cylinder unit 47 from the represented position in the direction of the arrow 46" into the position 46' represented by the broken lines. By means of the pivotably mounted flap 46 on the one hand the supply shaft 35 can be connected to the shaft 45 of the discharge apparatus 50 and on the other hand the supply shaft 35 can be connected to the shaft portion 33.

The discharge apparatus 50 comprises the shaft 45 provided with a venting and ventilating valve 48 and further shaft portions 45' and 45" arranged in not shown manner thereon. Between the two shaft portions 45',45" is provided a third sluice 55, which is provided with a closing element 52 operable by an associated piston/cylinder unit 51. With one shaft portion 45' constructed as a draining element is associated a reception tank 53 and with the second shaft portion 45" is associated a reception tank 54 for the drained fermented matter.

To the third, upwardly sloping portion 33 of the supply shaft 35 is fixed in not shown manner the conveying shaft 60. The conveying shaft 60 which is essentially constructed as a heat exchanger comprises a first, a second and a third shaft portion 61,62,63. With the third shaft portion 63 the conveying shaft 60 is fixed to a filling connection 64 of the tank 70 provided with a flange 64'. On the second and third shaft portions 62,63 is provided a heatable jacket 65 which, accompanied by the interposing of a pump 67, is connected via lines 66,66' to the boiler 85.

The stirrer 75 is located in the preferably e.g. horizontally positioned tank 70. The stirrer 75 comprises an axle body 69 axially passing through the tank and which is correspondingly rotatable about its longitudinal axis on the not shown side walls of the tank 70. The axle body 69 is provided with several, axially and radially reciprocally displaced stirring elements 71,72,73 and 74, which are fixed in not shown manner to said axle body 69.

At at least one end passing through the tank side wall, the axle body 69 is operatively connected with a correspondingly associated and constructed drive 76. By means of the drive 76 constructed e.g. as a piston drive and operatively connected via a lever bar 76' to the axle body 69, the stirrer 75 is driven in the direction of arrow R about the not shown or designated longitudinal axis of the axle body 69.

On the tank 70 is also provided a heatable jacket 82, which is connected via lines 81',81" and an interposed pump 81 to the boiler 85. With the boiler 85 is associated a tank 83 (oil tank), from which fuel is correspondingly supplied via a line 84' and accompanied by the interposing of a pump 84.

At its top the tank 70 is provided with at least one connecting piece, to which is connected a line 77' linked with a safety device 79. The safety device 79 e.g. constructed as an overpressure and underpressure valve is connected via a line 79' to the intermediate gas tank 80 for the supply of gaseous fuel via a line 80' and accompanied by the interposing of a blower 78 and which is connected via a line 78' to the boiler 85. The gas in the tank 80 can also be supplied via a line 80" to another, not shown energy supply installation.

In the lower region the tank 70 is provided with at least one outlet or discharge connection 57, which is connected in not shown manner to a correspondingly associated and constructed connecting piece 32' of the shaft portion 32.

It is pointed out here that the tank or fermenter 70 is preferably horizontally positioned in order to obtain an optimum process sequence, the filling connection 64 positioned approximately tangentially in the upper region of the tank 70 being located at one end and the outlet connection 57 in the lower region of the tank 70 is positioned at the other end. The stirring elements 71,72,73 and 74 arranged in reciprocally spaced manner on the axle body 69 are so constructed and displaced with respect to one another that during the stirring and mixing process the fermented matter is conveyed from one end of the tank 70 in the direction of the outlet connection 57 located at the other end thereof.

FIG. 2 shows as a second embodiment a portion of the diagrammatically represented installation 200. The elements not shown in FIG. 2 are constructed and positioned in substantially the same way as in the installation 100 described relative to FIG. 1.

The installation 200 comprises a first and a second conveyor belt 118, 118', an interposed comminuting apparatus 120, a supply shaft 135, a conveying shaft 160, a tank or fermenter 170 with a heating jacket 182 and a discharge apparatus 150 associated with said tank 170. The tank 170 contains a stirrer 175, which is constructed substantially identically to the stirrer 75 described relative to FIG. 1. The stirrer 175 is operatively connected to an axle body 169 driven in rotary manner about its longitudinal axis.

With the first conveyor belt 118 is associated a tank 117 from which the organic substances are supplied in the direction of arrows 119 and 119' to the comminuting apparatus 120 provided with two contrarotating roll bodies 123,124. The comminuted substances are supplied to a tank 117' and from there via the second conveyor belt 118' to a correspondingly constructed collecting tank 127 in accordance with arrow 119".

The collecting tank 127 is flanged in not shown manner to a portion 132 of the supply shaft 135. With the collecting tank 127 is associated a feeder 149 operable by a piston/cylinder unit 148 and by means of which the substances are forced into and compressed in the chamber 127'. In a portion 131 of the supply shaft 135 is provided a thrust element 139 linearly displaceable in the direction of arrows X,X' and which is operatively connected to a piston/cylinder unit 138.

The supply shaft 135 is flanged by portion 132 to a correspondingly associated and roughly vertically oriented portion 162 of the conveying shaft 160. A sluice or lock 130 is positioned between the two portions 132,162 and has a closing element 128 operable by a piston/cylinder unit 129.

The conveying shaft 160 e.g. provided with two heated jacket parts 165, 165' is flanged in the upper region by a portion 163 to a filling connection 164 of the tank 170 and in the lower region by a portion 161 to a portion 133 of a discharge shaft 145. Between the two portions 161 and 133 is located a sluice 140, which has a closing element 142 operable by a piston/cylinder unit 141.

The conveying shaft 160 is essentially constructed as a heat exchanger and is correspondingly heated by the two jacket parts 165,165' connected via supply and return lines 166,166',166" to a not shown boiler.

In the lower region the tank 170 is provided with at least one outlet or discharge connection 157, which is connected to a shaft portion 135'. The discharge shaft 145 located on the shaft portion 135' comprises a first portion 145' and a second portion 145", whilst between the discharge shaft 145 and the first portion 145', as well as between the first portion 145' and the second portion 145" is in each case provided a sluice 155 or 155'. The sluice 155 has a closing element 152 operable by a piston/cylinder unit 151 and the e.g. identically constructed sluice 155' has a closing element 152' operable by a piston/cylinder unit 151'.

In the shaft portion 135' and in the discharge shaft 145 of the discharge apparatus 150 is provided a thrust element only represented partly by broken lines here and which is linearly displaceable for different functional steps by a not shown piston/cylinder unit and can be positioned in different positions. The individual positions B',C',D' and E' of the front portion 139' of the thrust element shown in broken line form in FIG. 2 will be described in conjunction with the operation of the overall installation 200.

The two aforementioned installations 100 and 200 can be supplied with all possible organic substances for utilization and processing and examples thereof are given hereinafter:

green matter, such as e.g. lawn clippings, foliage, shrubs and the like;

organic waste, such as e.g. obtained in the case of separated or sorted refuse collection;

vegetable and fruit waste;

kitchen and in particular commercial kitchen, canteen and similar waste;

waste from slaughter houses, e.g. rumens, intestine contents, etc.;

waste from the food industry.

These substances can be supplied to the installations 100 or 200 for utilization purposes.

The tank 70 or 170 is mounted approximately horizontally on two spaced, not shown foundations in the axial direction of the particular tank. In a preferred arrangement of the tank 70 or 170 on foundations the mounting support is provided with a gradient from the filling connection 64 or 164 in the direction of the outlet connection 57 or 157.

The essential working steps for the installation 100 will now be described. The comminuted organic substance compressed by the conveyor screw 25 in the chamber 27 will subsequently be referred to as fresh material and the matter obtained after passing through the specific process stages and discharged from the tank 70 or fermenter will be called fermented matter.

In a first phase the compressed fresh material from the conveyor screw 25 and with the sluice 30 open passes into portion 32 of the supply shaft 35 and is subsequently conveyed by the thrust element 39 e.g. by a control means in operative connection with the sluice 30 in the direction of arrow X. This process is repeated e.g. intermittently several times with the sluice 40 open and the discharge apparatus 50 closed until the conveying shaft 60 constructed as a heat exchanger is filled to roughly in the vicinity of the filling connection 64.

Filling can be monitored by correspondingly positioned, not shown sensing elements and the further fresh material supply can be correspondingly controlled. Then, with the sluice 40 closed, the fresh material particularly located in the vicinity of the heated jacket 65 of the conveying shaft 60 is heated. On reaching a given temperature and with the sluice 30 closed and the sluice 40 open new fresh material is supplied by the thrust element 39, so that simultaneously an approximately equal quantity of the heated fresh material in the conveying shaft 60 passes in the direction of the arrow Z into the also heated tank 70 and is thoroughly mixed by the stirrer 75 in operative connection With the drive 76.

The correspondingly controllable process and operating temperature is chosen in accordance with the composition of the fresh material supplied and in the mesophilic range is approximately 28° to 38° C. and in the thermophilic range approximately 50° to 60° C.

During the mixing process in the tank or fermenter 70, the methane formers given off are supplied through the movement of the stirrer 75 to the fresh material introduced and consequently the metabolic conversion is accelerated. Through the movement and through bacterial decomposition the fermenter content (fresh material and fermented matter mixture) is freed from organic solids and liquefied, so that there is a volume reduction of approximately 35 to 50%.

The gas formed in the tank or fermenter 70 is supplied via the line 77' located on the connecting piece 77 and connected to the interior of the tank 70 to the intermediate gas reservoir 80, so that an inflation of the fermented matter in the tank 70 is prevented. The gas is supplied from the gas reservoir 80 to the boiler 85 for generating energy. The gas formed during the fermentation process in the fermenter 70 can consequently be advantageously used as process energy for operating the boiler 85. However, the gas in the reservoir 80 can also be supplied via a line 80" to a not shown energy supply installation.

In an intermediate phase the thrust element 39 is moved back into the position A opening the outlet connection 57 of the tank 70, so that with the sluice 30 closed a specific fermented matter quantity can be conveyed from the tank 70 as so-called bacterial inoculum into the portion 32 of the supply shaft 35.

The proportional ratio of the supplied bacterial inoculum with respect to the fresh material introduced into the portions 32,33 of the supply shaft 35 is e.g. determined as a function of the composition and characteristics of the fresh material and inoculum.

The bacterial inoculum is forced by the thrust element 39 in the direction of arrow X into the position C and to the fresh material located in portions 32 and 33 and subsequently is pressed into the conveying shaft 60 with the sluice 40 open. During this process simultaneously the quantity in the conveying shaft is supplied in the direction of arrow Z to the tank 70, whilst the fresh material compressed with the bacterial inoculum during this process is heated in the conveying shaft 60 with the sluice 40 closed.

In the final phase, in which the thrust element 39 has moved back in the direction of arrow X' into position A, the fermented matter is conveyed from the tank into the portion 32 and subsequently is moved by the thrust element 39, with the flap 46 open (broken line position) into the discharge apparatus 50. During this process the sluice 55 initially remains closed, so that in this phase the fermented matter is compressed and drained at a predetermined and correspondingly monitored pressure of the thrust element 39. The water is received by the associated tank 53. As soon as the thrust element 39 has reached the position E, the sluice 55 is opened, so that the compressed fermented matter drops into the associated tank 54. Prior to the moving back of the thrust element 39 the sluice 55 of the discharge apparatus 50 is closed again.

The fermented matter obtained in the aforementioned process can subsequently be used as an additive for compost, garden mould, etc.

Diverging from the working steps described by means of the installation 100 of FIG. 1, in the case of installation 200 according to FIG. 2 the comminuted organic material is substantially directly forced by the thrust element 139 into the conveying shaft 160 constructed as a heat exchanger. The fresh material compressed by the feeder 149 passes into portion 132 of the supply shaft 135 with the sluice 130 open and is subsequently conveyed by the thrust element 139, e.g. by a control means in operative connection with the sluice 130 in the direction of arrow X. This process is intermittently repeated several times with the sluice 140 closed until the conveying shaft 160 is filled approximately to the area of the filling connection 164.

The further operating and process steps of the installation 200 are substantially identical to those described hereinbefore in conjunction with the installation 100 according to FIG. 1.

In the embodiment of the installation 200 shown in FIG. 2 it is apparent that the individual supply shafts 135 and 135' are so separated from one another that there is no possibility of a mixing or infecting of the substantially sterile fermented matter with the fresh material.

While the invention has been particularly shown and described with respect to the preferred embodiments thereof, it should be understood by those skilled in the art that the foregoing and other changes in form and details may be made therein without departing from the spirit and scope of the invention which should be limited only by the scope of the appended claims.

We claim:

1. A process for producing utilizable compost from waste materials, comprising the sequential steps of:
sorting out fresh organic substances from the waste materials;
crushing said fresh organic substances;
pressing said fresh organic substances in a closable chamber;
transferring said pressed substances into a supply shaft;
shifting said pressed substances portion by portion from said supply shaft into a conveying shaft and filling said conveying shaft up to an inlet of a fermenting tank;
heating said pressed substances in said conveying shaft;
introducing said heated substances into said fermenting tank by shifting additional fresh substances portion by portion from said supply shaft into said conveying shaft;
agitating said heated substances in said fermenting tank for mixing fresh and fermented substances and for decomposing said substances;
discharging a portion of said decomposed substances into said supply shaft and shifting said portion into said conveying shaft for introducing said portion into said fresh substances; and
separating the connection of said supply shaft to the conveying shaft and discharging the remaining decomposed substances via said supply shaft and an outlet shaft.

2. A process for producing utilizable compost from waste materials, comprising the sequential steps of:
sorting out fresh organic substances from the waste materials;
crushing said fresh organic substances;
pressing said fresh organic substances in a closable chamber;
shifting said pressed substances portion by portion from said chamber into a conveying shaft and filling said conveying shaft up to an inlet of a fermenting tank;
heating said pressed substances in said conveying shaft;

introducing said heated substances into said fermenting tank by shifting additional fresh substances portion by portion into said conveying shaft;

agitating said heated substances in said fermenting tank for mixing fresh and fermented substances and for decomposing said substances;

discharging a portion of said decomposed substances into a supply shaft and shifting said portion into said conveying shaft for introducing said portion into said fresh substances; and separating the connection of said supply shaft to the conveying shaft and discharging remaining decomposed substances via said supply shaft and an outlet shaft.

3. The process of claim 1, including maintaining a process temperature in the fermenting tank in the thermophylic range of from approximately 50° to 60° C., methane formers formed during the fermenting being used for accelerating the fermentation process and being discharged for producing heat and energy.

4. The process of claim 2, including maintaining a process temperature in the fermenting tank in the thermophylic range of from approximately 50° to 60° C., methane formers formed during the fermenting being used for accelerating the fermentation process and being discharged for producing heat and energy.

* * * * *